United States Patent
Pettit et al.

(10) Patent No.: US 12,089,894 B2
(45) Date of Patent: Sep. 17, 2024

(54) PREDICTION OF POST-OPERATIVE VIGNETTING IN A PSEUDOPHAKIC EYE

(71) Applicant: ALCON INC., Fribourg (CH)

(72) Inventors: George Hunter Pettit, Fort Worth, TX (US); Mark Andrew Zielke, Lake Forest, CA (US); Victor Manuel Hernandez, Fort Worth, TX (US); Philip Matthew McCulloch, Mansfield, TX (US)

(73) Assignee: Alcon Inc., Fribourg (CH)

( * ) Notice: Subject to any disclaimer, the term of this patent is extended or adjusted under 35 U.S.C. 154(b) by 526 days.

(21) Appl. No.: 17/501,894

(22) Filed: Oct. 14, 2021

(65) Prior Publication Data
US 2022/0183547 A1 Jun. 16, 2022

Related U.S. Application Data

(60) Provisional application No. 63/124,281, filed on Dec. 11, 2020.

(51) Int. Cl.
*A61B 3/00* (2006.01)
*A61B 3/103* (2006.01)
*A61B 3/11* (2006.01)

(52) U.S. Cl.
CPC .......... *A61B 3/0025* (2013.01); *A61B 3/0008* (2013.01); *A61B 3/103* (2013.01); *A61B 3/112* (2013.01)

(58) Field of Classification Search
CPC ..... A61B 3/0025; A61B 3/0008; A61B 3/103; A61B 3/112
See application file for complete search history.

(56) References Cited

U.S. PATENT DOCUMENTS

| 7,217,289 B2* | 5/2007 | Coronco | A61F 2/1613 351/159.6 |
| 10,743,985 B2* | 8/2020 | Olsen | A61B 5/0082 |

(Continued)

OTHER PUBLICATIONS

Jack T Holladay et al: "Negative dysphotopsia: The enigmatic penumbra", Journal Cataract and Refractive Surgery, Surgery, Fairfax, VA, US, vol. 38, No. 7, Jan. 29, 2012 (Jan. 29, 2012), pp. 1251-1265, XP028496416, ISSN: 0886-3350, DOI: 10.1016/J.JCRS.2012.01.032 [retrieved on Apr. 19, 2012] p. 1252-p. 1253.

(Continued)

*Primary Examiner* — Tuyen Tra

(57) ABSTRACT

A system for predicting post-operative vignetting in an eye of a subject includes a controller having a processor and a tangible, non-transitory memory on which instructions are recorded. The controller is in communication with a diagnostic module adapted to store pre-operative anatomic data of the eye as an eye model. The system includes a projection module and a ray tracing module selectively executable by the controller. The projection module is adapted to determine imputed post-operative variables of the eye based at least partially on the pre-operative anatomic data and the intraocular lens. The ray tracing module is adapted to calculate propagation of light through the eye. The ray tracing module is executed to determine a light distribution for respective visual field angles across a predefined field of view. The controller is configured to determine one or more post-operative vignetting parameters based at least partially on the light distribution.

18 Claims, 3 Drawing Sheets

(56) References Cited

U.S. PATENT DOCUMENTS

2007/0276482 A1   11/2007   Coroneo
2013/0345807 A1   12/2013   Olsen

OTHER PUBLICATIONS

Xin Hong et al: "Ray-tracing optical modeling of negative dysphotopsia", Journal of Biomedical Optics, vol. 16, No. 12, Jan. 1, 2011 (Jan. 1, 2011), p. 125001, XP055663682, 1000 20th St. Bellingham WA 98225-6705 USA ISSN: 1083-3668, DOI: 10.1117/1.3656745 pp. 1-2.
Erie Jay C et al: "Effect of a sulcus-fixated piggyback intraocular lens on negative dysphotopsia: Ray-tracing analysis", Journal Cataract and Refractive Surgery, vol. 45, No. 4, Apr. 2019 (Apr. 2019), pp. 443-450, XP085649570, ISSN: 0886-3350, DOI: 10.1016/J. JCRS.2018.10.041 p. 443-p. 445.
Masket, MD, et al., Surgical management of negative dysphotopsia, Journal of Cataract and Refractive Surgery, Oct. 20, 2017, pp. 6-16, 44-1, Elsevier Inc.
Vught, et al., Distinct differences in anterior chamber configuration and peripheral aberrations in negative dysphotopsia, Journal of Cataract and Refractive Surgery, Mar. 19, 2020, pp. 1007-1015, 46-7, Wolters Kluwer Health, Inc. on behalf of ASCRS and ESCRS.

\* cited by examiner

PREDICTION OF POST-OPERATIVE VIGNETTING IN A PSEUDOPHAKIC EYE

INTRODUCTION

The disclosure relates generally to predicting post-operative vignetting in an eye of a subject, prior to the eye being implanted with an intraocular lens. More specifically, the disclosure relates to a system and method for obtaining one or more post-operative vignetting parameters of a pseudophakic eye (an eye having an implanted lens). The human lens is generally transparent such that light may travel through it with ease. However, many factors may cause areas in the lens to become cloudy and dense, and thus negatively impact vision quality. The situation may be remedied via a cataract procedure, whereby an artificial lens is selected for implantation into a patient's eye. Indeed, cataract surgery is commonly performed all around the world. After cataract surgery, a number of patients experience negative dysphotopsia, a condition characterized by dark shadows in the peripheral field of view of the patient. This shadow is believed to be due to vignetting of light in the pseudophakic eye. In some cases, the phenomenon persists long after surgery. Some cases may require secondary surgical intervention. At present there is no objective means of determining, prior to the cataract surgery, the individual risk for a patient of developing some type of negative dysphotopsia and its potential severity.

SUMMARY

Disclosed herein is a system for predicting post-operative vignetting in an eye of a subject prior to implantation with an intraocular lens. The system includes a controller having a processor and a tangible, non-transitory memory on which instructions are recorded. The controller is in communication with a diagnostic module adapted to store pre-operative anatomic data of the eye as an eye model. The system includes a projection module and a ray tracing module selectively executable by the controller. The projection module is adapted to determine imputed post-operative variables of the eye based at least partially on the pre-operative anatomic data and the intraocular lens. The ray tracing module is adapted to calculate propagation of light through the eye. The controller is configured to obtain the pre-operative anatomic data of the eye, via the diagnostic module. The controller is configured to determine imputed post-operative variables of the eye, via the projection module, and incorporate the imputed post-operative variables into the eye model. The ray tracing module is executed to determine a light distribution for respective visual field angles across a predefined field of view in the eye model. The controller is configured to determine one or more post-operative vignetting parameters based at least partially on the light distribution for the respective visual field angles.

The ray tracing module traces a bundle of rays propagating through the eye. The post-operative vignetting parameters may include a first visual angle defined as a smallest of the respective visual field angles where at least a portion of the bundle of rays passing through a pupil of the eye will not pass through an optical zone of the intraocular lens. The post-operative vignetting parameters may include a second visual angle defined as the smallest of the respective visual field angles where the bundle of rays passing through the pupil will not pass through the optical zone of the intraocular lens. The post-operative vignetting parameters may include a third visual angle defined as the smallest of the respective visual field angles where the bundle of rays passing through the pupil will miss the intraocular lens entirely.

In some embodiments, the pre-operative anatomic data includes an axial length of the eye. The pre-operative anatomic data may include a respective location and a respective profile of an anterior corneal surface and a posterior corneal surface of the eye. The pre-operative anatomic data may include a location, an orientation, and a size of a pupil of the eye in a three-dimensional coordinate system, the pupil being under photopic conditions. The imputed post-operative variables of the eye may include a respective location and a respective orientation of the intraocular lens. The imputed post-operative variables of the eye may include a respective location and a respective orientation of a pupil and/or iris of the eye.

In some embodiments, the ray tracing module is adapted to trace a bundle of rays propagating posteriorly through the intraocular lens until reaching a retina of the eye. The bundle of rays is focused to an infinitesimally small spot on the retina. The ray tracing module may be adapted to employ respective refractive indices in the eye applicable to a wavelength of 550 nanometers of light.

Disclosed herein method for predicting post-operative vignetting in an eye of a subject prior to implantation with an intraocular lens, with a system having a controller with a processor and a tangible, non-transitory memory on which instructions are recorded. The method includes adapting a diagnostic module to store pre-operative anatomic data of the eye as an eye model, via at least one imaging device. A projection module is adapted to determine imputed post-operative variables of the eye based at least partially on the pre-operative anatomic data and the intraocular lens, via the controller.

The method includes adapting a ray tracing module to calculate propagation of light through the eye, the ray tracing module being selectively executable by the controller. Pre-operative anatomic data of the eye is obtained, via the diagnostic module. The method includes determining imputed post-operative variables of the eye, via the projection module, and incorporating the imputed post-operative variables into the eye model. The ray tracing module is executed to determine a light distribution for respective visual field angles across a predefined field of view in the eye model. The method includes determining one or more post-operative vignetting parameters based at least partially on the light distribution for the respective visual field angles.

The above features and advantages and other features and advantages of the present disclosure are readily apparent from the following detailed description of the best modes for carrying out the disclosure when taken in connection with the accompanying drawings.

DETAILED DESCRIPTION

Figure 1:
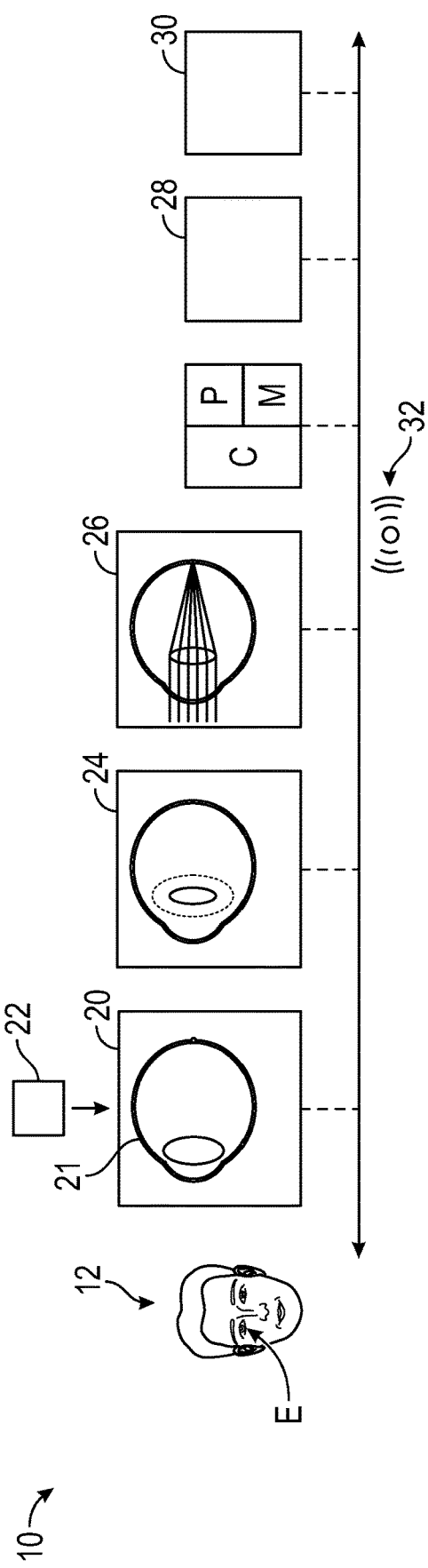
FIG. 1 is a schematic illustration of a system for predicting post-operative vignetting in an eye, the system having a controller.

Referring to the drawings, wherein like reference numbers refer to like components, FIG. 1 schematically illustrates a system 10 for predicting parameters related to post-operative vignetting in an eye E, for a subject 12 that is a candidate for cataract surgery. It is understood that the drawings are intended to be illustrative and are not drawn to scale. Referring to FIG. 1, the system 10 includes a controller C having at least one processor P and at least one memory M (or non-transitory, tangible computer readable storage medium) on which instructions are recorded for executing method 100, which is described in detail below with reference to FIG. 2. The memory M can store controller-executable instruction sets, and the processor P can execute the controller-executable instruction sets stored in the memory M.

Post-operative vignetting is a partial shadowing in a field of view or image plane occurring in the subject 12 after cataract surgery. Vignetting may be described as image dimming or a loss in image brightness perceived by the subject 12 and is usually seen at the edges of the image. Vignetting occurs due to light encountering an aperture and becoming partially or totally blocked before reaching the image plane. In some situations, a portion of the incident light is blocked while another portion of the light persists through the optical system. Here, the remaining light continues to form the image but is less bright than it otherwise would be. Post-operative vignetting is associated with negative dysphotopsia, a condition which may require secondary surgical intervention.

Figure 3:
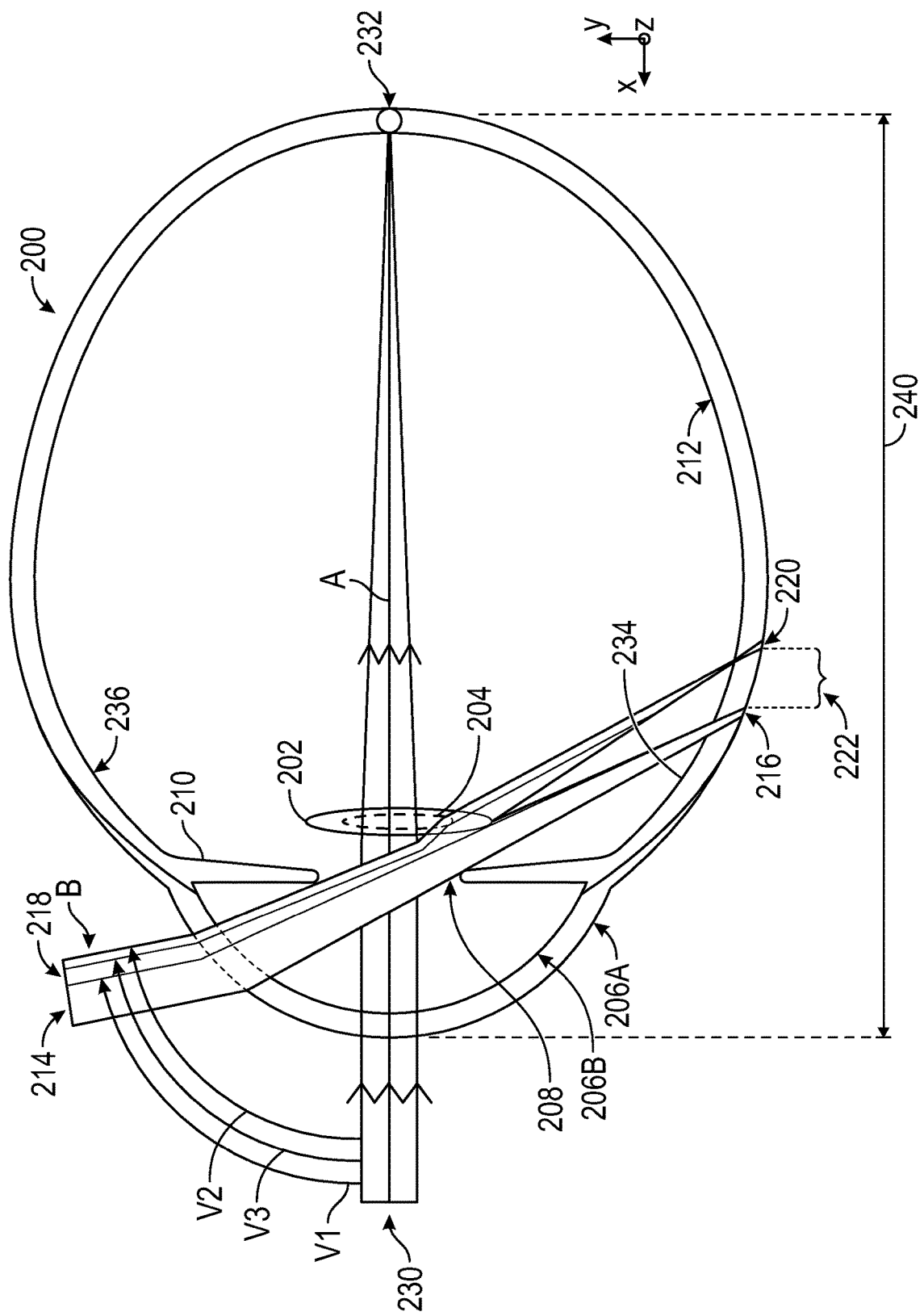
FIG. 3 is a schematic fragmentary diagram of an example model of a pseudophakic eye, illustrating post-operative vignetting.

FIG. 3 is a schematic diagram illustrating post-operative vignetting in a pseudophakic eye 200. The pseudophakic eye 200 has an intraocular lens 202 with an optical zone 204, which is the effective focusing or refractory portion of the intraocular lens 202. Also shown in FIG. 3 are the anterior corneal surface 206A, posterior corneal surface 206B, pupil 208, iris 210, retina 212 and visual axis A. Referring to FIG. 3, a beam B enters the pupil 208 at a relatively large visual field angle. The pupil 208 and iris 210 act as a system stop to define the extent of light forming the image perceived by the subject 12. While the entire beam B travels through the pupil 208, some portions of it do not traverse the intraocular lens 202.

Referring to FIG. 3, a first beam portion 214 of the beam B misses the optical zone 204 entirely and passes directly to the retina 212 at the first retinal location 216. A second beam portion 218 passes through the intraocular lens 202 and is focused at a second retinal location 220. Between the first retinal location 216 and the second retinal location 220 is an intermediate retinal location 222 that will not be illuminated at all by the beam B. Although the second retinal location 220 is illuminated, it is only partially so because only a fraction of the beam B at this angle is focused by the intraocular lens 202, i.e. the fraction that passes through the optical zone 204.

The combination of the second retinal location 220 and the intermediate retinal location 222 may be perceived by the subject 12 as a dark shadow. This dark shadow may be accentuated by the brighter illumination in the second retinal location 220. In the embodiment shown in FIG. 3, the subject 12 will perceive the first retinal location 216 as occurring at a larger visual field angle than the second retinal location 220, even though the light causing both comes from a single direction.

The system 10 (via execution of the method 100) provides an assessment as to the potential severity of vignetting in the pseudophakic eye 200 based on pre-operative information. The technical advantage of the system 10 is that the clinician will have this information before cataract surgery and may counsel the subject 12 appropriately and adjust the treatment plan (e.g., type of implant, implant location, optical power) if appropriate.

As described below, referring to FIG. 1, the system 10 may include a diagnostic module 20 to store pre-operative anatomic data of the eye E. The pre-operative anatomic data may be obtained from at least one imaging device 22. The system 10 may include a projection module 24 and a ray tracing module 26 selectively executable by the controller C. The projection module 24 is adapted to predict post-operative anatomic parameters of the eye E based at least partially on the pre-operative anatomic data. The ray tracing module 26 is adapted to trace a bundle of rays 230 propagating through the pseudophakic eye 200, as described below.

Referring to FIG. 1, the system 10 may include a user interface 28 operable by a user. The user interface 28 may include a touchscreen or other input device. The controller C may be configured to process signals to and from the user interface 28 and a display (not shown). Additionally, the user interface 28 and/or the controller C may be in communication with a lens selection module 30.

The various components of the system 10 may be configured to communicate via a network 32, shown in FIG. 1. The diagnostic module 20, projection module 24 and ray tracing module 26 may be embedded in the controller C. Alternatively, the diagnostic module 20, projection module 24 and ray tracing module 26 may be a part of a remote server or cloud unit accessible to the controller C via the network 32. The network 32 may be a bi-directional bus implemented in various ways, such as for example, a serial communication bus in the form of a local area network. The local area network may include, but is not limited to, a Controller Area Network (CAN), a Controller Area Network with Flexible Data Rate (CAN-FD), Ethernet, WIFI, Bluetooth™ and other forms of data connection. Other types of connections may be employed.

Figure 2:
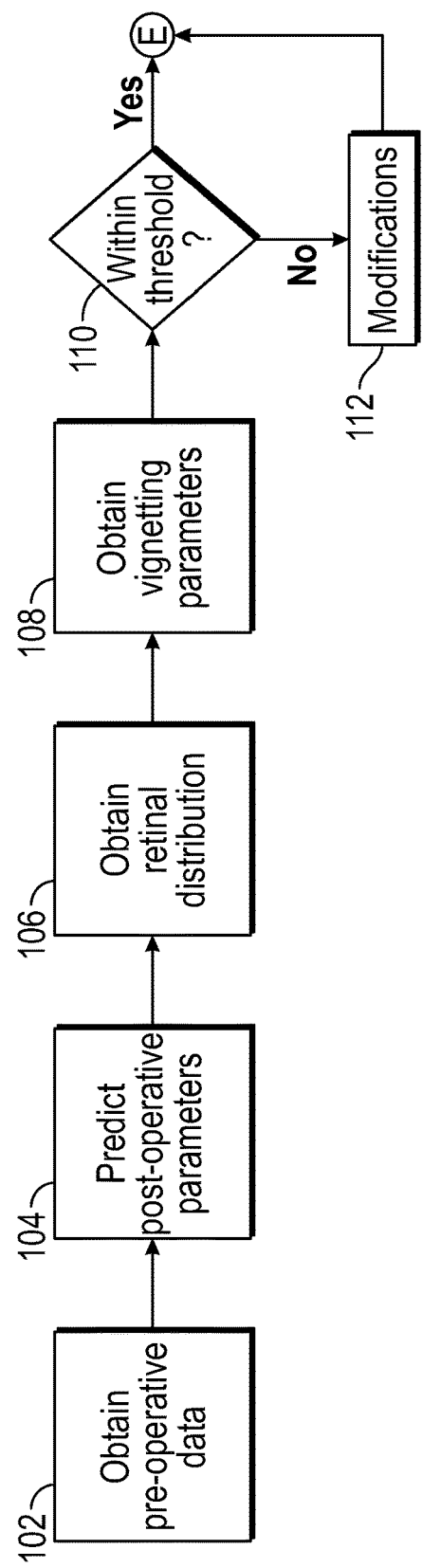
FIG. 2 is a schematic flowchart of a method executable by the controller of FIG. 1.

Referring now to FIG. 2, a flow chart of the method 100 for predicting post-operative vignetting in the pseudophakic eye 200 is shown. Method 100 may be fully or partially executable by the controller C of FIG. 1. Method 100 need not be applied in the specific order recited herein. Additionally, it is understood that some blocks may be omitted. The method 100 begins at block 102.

Per block 102 of FIG. 2, the controller C is configured to obtain pre-operative anatomic data of the eye E, which may be stored as part of an eye model 21 in a diagnostic module 20. The pre-operative anatomic data (which include biometric data) may be obtained from at least one imaging device 22. The imaging device 22 may include a topography device, an ultrasound machine, optical coherence tomography machine, a magnetic resonance imaging machine or other imaging device available to those skilled in the art. The pre-operative anatomic data may be derived from a single image or from multiple images.

Figure 4:
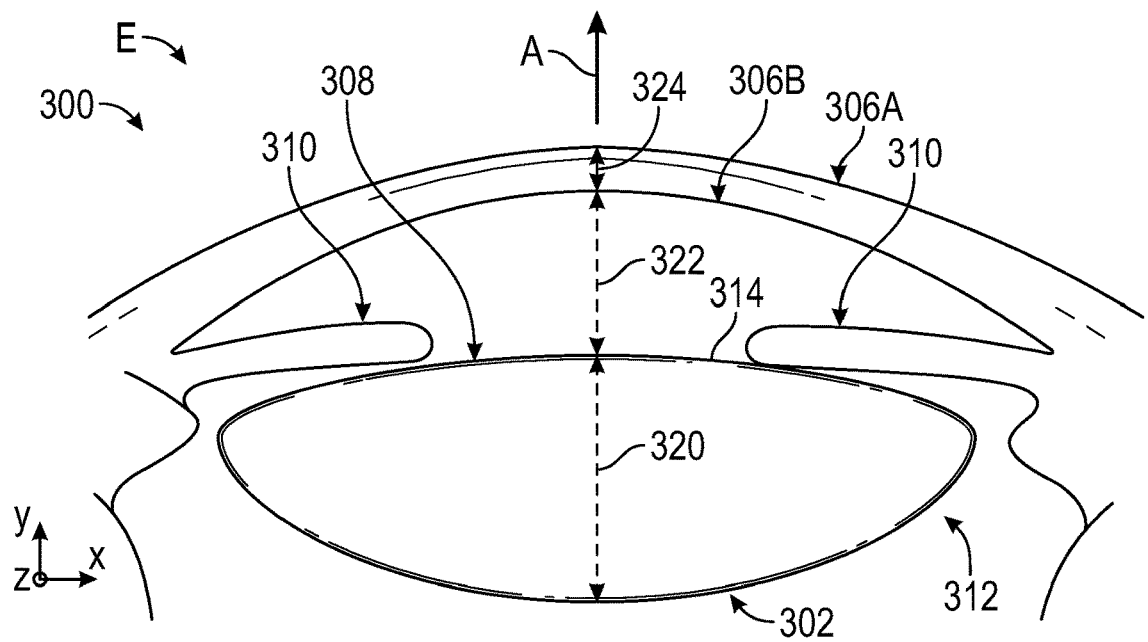
FIG. 4 is a schematic fragmentary cross-sectional view of an example pre-operative image of the eye.

FIG. 4 shows a schematic example of a pre-operative image 300 of the eye E containing a natural lens 302. The pre-operative image 300 may be obtained via an ultrasound bio-microscopy technique. The ultrasound bio-microscopy technique may employ a relatively high frequency transducer of between about 35 MHz and 100 MHz, with a depth of tissue penetration between about 4 mm and 5 mm. Referring to FIG. 4, the pre-operative anatomic data include a respective position, respective orientation, and size of the pupil 308 under photopic conditions. Photopic conditions refer to vision under well-lit conditions, which functions primarily due to cone cells in the eye. In some embodiments, photopic conditions may be defined to cover adaptation levels of 3 candelas per square meter ($cd/m^2$) and higher.

Referring to FIG. 4, the pre-operative anatomic data include a respective position and respective orientation of the iris 310 and natural lens 302. The respective orientation includes a tilt relative to an XYZ coordinate system. The respective positions of the pupil 308, iris 310 and natural lens 302 may be specified in three dimensions in an XYZ coordinate system; along the X axis as well as along the Y axis and Z axis. The XYZ coordinate system may be defined such that the X axis is parallel to the visual axis A. Alternatively, the XYZ coordinate system may be defined such that the X axis is parallel to another geometrical or optical axis (not shown). Here, the eye model 21 would include the position and orientation of the visual axis A.

Referring to FIG. 4, the pre-operative anatomic data may include lens thickness 320, anterior chamber depth 322 and corneal thickness 324. In addition, the eye model 21 in the diagnostic module 20 contains the refractive indices of the different portions of the eye E. The pre-operative anatomic data include an axial length 240 (shown in FIG. 3) of the eye E.

The diagnostic module 20 may be selectively executable to approximate or parametrize surfaces in the eye E based on the pre-operative anatomic data and algorithms available to those skilled in the art. The eye model 21 of FIG. 1 may include the shape and location of the anterior corneal surface 306A and the posterior corneal surface 306B (see FIG. 4) over the full region where light of interest may enter the eye E. The eye model 21 may further include the shape and location of the anterior lens surface 314 and the posterior lens surface 312 (see FIG. 4). The eye model 21 may approximate the surface of the retina 212 (shown in FIG. 2) from the axial length 240 as the ocular globe typically has a near spherical shape.

The method 100 proceeds to block 104 from block 102. Per block 104, the controller C is configured to determine imputed post-operative variables of the eye E, based in part on the pre-operative anatomic data. The imputed post-operative variables may be obtained through a projection module 24. In some embodiments, the projection module 24 incorporates intraocular lens power calculation formula available to those skilled in the art such as for example, the SRK/T formula, the Holladay formula, the Hoffer Q formula, the Olsen formula and the Haigis formula. In other embodiments, the projection module 24 incorporates a machine learning module, such as a neural network, which is trained to determine the imputed post-operative variables through a large number of historical pairs of pre-operative data and post-operative data. Historical pairs refers to pre-operative data and post-operative data of the same person (e.g., FIGS. 4 and 5). It is understood that the imputed post-operative variables may be obtained from other estimation methods available to those skilled in the art.

Figure 5:
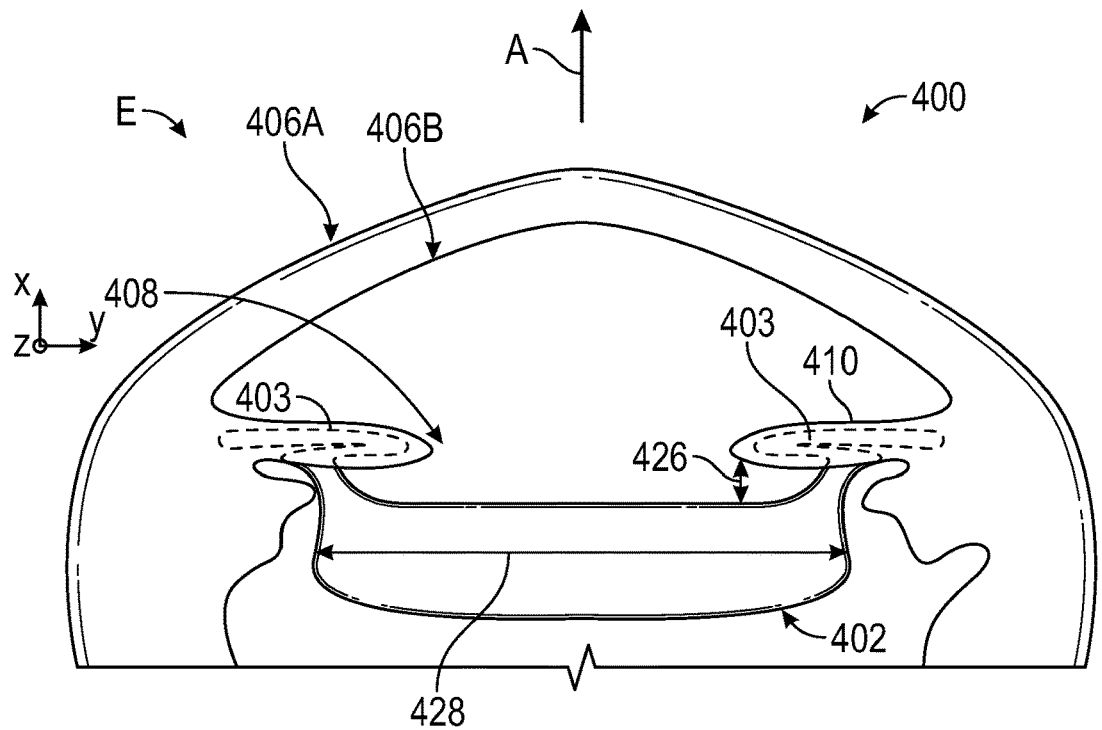
FIG. 5 is a schematic fragmentary cross-sectional view of an example post-operative image of the eye.

FIG. 5 shows a schematic example of a post-operative image 400 of the eye E. Also shown in FIG. 5 is the intraocular lens 402 with supporting structure or haptics 403, anterior corneal surface 406A, posterior corneal surface 406B, pupil 408 and iris 410. The imputed post-operative variables include a respective location and a respective orientation or tilt (relative to the XYZ coordinate system) of the intraocular lens 402, the pupil 408 and/or the iris 410. Post-operatively, the pupil 408 may be decentered or tilted with respect to the visual axis A. In the pre-operative image 300, the iris 310 may be bulging and shifted anteriorly (relative to the post-operative image 400) due to the relatively bulkier shape of a natural lens 302. In the post-operative image 400, the iris 410 may assume a relatively more planar geometry.

The method 100 proceeds to block 106 from block 104. Per block 106 of FIG. 2, the controller C is configured to determine a light distribution across a predefined field of view for the eye E, based on the data obtained in blocks 102 and 104. Referring to FIG. 3, the predefined field of view may be defined as an arc along the retina 212, between starting retinal location 234 and ending retinal location 236. The light distribution may be obtained via the ray tracing module 26 (see FIG. 1). Referring to FIG. 3, the ray tracing module 26 (of FIG. 1) is adapted to trace a bundle of rays 230 propagating through the anterior corneal surface 206A and posterior corneal surface 206B of the pseudophakic eye 200.

The bundle of rays 230 of FIG. 3 are propagated posteriorly through the intraocular lens 202 until reaching the retina 212. The ray tracing module 26 employs the eye model 21 (from block 102) substituted with the imputed post-operative variables obtained in block 104 (such as the respective position and respective tilt of the pupil 208, iris 210 and intraocular lens 202). Optionally, the ray tracing module 26 may assume that effects related to the wave nature of light may be neglected such that the propagation of light is described in terms of rays.

The propagation is traced through reflection and refraction using Snell's law, which describes the refraction of a ray at a surface separating two media with different refractive indices. In other words, as a respective ray in the bundle of rays 230 encounters a surface, the new direction of the respective ray is determined in accordance with Snell's law using the refractive indices stored in the diagnostic module 20. In some embodiments, the ray tracing module 26 employs refractive indices applicable to 550 nm wavelength of light (green light). The bundle of rays 230 is focused to an infinitesimally small spot 232 at the retina 212 and the spatial distribution of the bundle of rays 230 on the retina 212 is recorded. The spatial distribution may be represented by a point spread function graph along the retina 212.

The ray tracing module 26 provides an assessment of the focusing properties of the pseudophakic eye 200 by moving the bundle of rays 230 in increments to cover respective visual angles for the predefined field of view. As noted above, the predefined field of view may be defined as an arc along the retina 212, between starting retinal location 234 and ending retinal location 236. The light distribution reflects the amount of light hitting the retina 212 (making it through) as the incident angle of the bundle of rays 230 is varied. In areas of shadowing (such as at high visual angles), the spatial distribution of the bundle of rays 230 (represented by a point spread function graph) is flattened and/or bifurcated.

From block 106, the method 100 proceeds to block 108. Per block 108 of FIG. 2, the controller C is configured to determine one or more post-operative vignetting parameters of the pseudophakic eye 200 based on the light distribution obtained in block 106. The post-operative vignetting parameters include visual field angles for different regions in the retina 212. Referring to FIG. 3, the post-operative vignetting parameters include a first visual angle V1, a second visual angle V2 and a third visual angle V3.

Referring to FIG. 3, the first visual angle V1 is defined as the smallest of the respective visual field angles where at least a portion of the bundle of rays 230 passing through the pupil 208 will not pass through the optical zone 204 of the intraocular lens 202. The size of the first visual angle V1 indicates where vignetting likely will first begin. The second visual angle V2 is defined as the as the smallest of the respective visual field angles where the bundle of rays 230 passing through the pupil 208 will not pass through the optical zone 204 of the intraocular lens 202.

The second visual angle V2 indicates where light missing the intraocular lens entirely will be perceived. The third visual angle V3 is defined as the smallest of the respective visual field angles where the bundle of rays 230 passing through the pupil 208 will miss the intraocular lens 202 entirely. The third visual angle V3 indicates where the image perceived by the subject 12 may become completely black. The visual angles help to determine the impact of post-operative vignetting on the subject 12, including useful information as to likelihood and potential extent of negative dysphotopsia after cataract surgery.

The method 100 proceeds from block 108 to block 110. Per block 110, the controller C is configured to determine if the post-operative vignetting parameters obtained in block 108 are within respective predefined thresholds, i.e., separate thresholds for each factor. The respective thresholds may be defined or selected based on the application at hand and may vary based on the subject 12. In one example, the respective predefined thresholds are 75, 80 and 85 degrees, respectively, for the first visual angle V1, the second visual angle V2 and the third visual angle V3.

If the post-operative vignetting parameters are within the respective predefined thresholds, the method 100 is ended. If the post-operative vignetting parameters are not within respective predefined thresholds, the method 100 may proceed to block 112 to determine what modifications may be appropriate. For example, if the size of at least one of the first visual angle V1, the second visual angle V2 and the third visual angle V3 is below the respective predefined thresholds, the surgical plan may be altered to incorporate one or more alternative techniques to lessen the occurrence and/or severity. Because there are tradeoffs involved, the alternative techniques may not normally be pursued.

Referring to FIG. 5, the modifications may include decreasing the spacing 426 between the iris 410 and the intraocular lens 402. A decrease in distance between the body of the intraocular lens 402 and iris 410 will yield an improvement in vignetting. With an increased spacing 426, the intraocular lens 402 encounters less light and the field angle increases.

Referring to FIG. 5, the modifications may include using an intraocular lens 402 with a larger diameter 428. Increasing the diameter of the intraocular lens 402 places lens surfaces in current gaps. In one example, enlarging the diameter 428 of the intraocular lens 402 from 6 mm to 7 mm pushed the 70% throughput field of view from 81 to 83.5 degrees. This is approximately equivalent to moving a 6 mm lens forward by 100 microns, in one eye model. The modifications may further include implanting the intraocular lens 402 in the sulcus rather than the capsular bag.

If each of the first visual angle V1, the second visual angle V2 and the third visual angle V3 is below the respective threshold, the controller C may be configured to select a different intraocular lens (e.g. different model and/or optical power), via the lens selection module 30, and repeat the steps of the method 100. Additionally, clinicians may offer counselling and manage expectations.

In summary, the system 10 inputs pre-operative anatomic data of the eye E about to undergo cataract surgery, predicts various post-operative anatomic parameters and uses ray tracing optical analysis to calculate various parameters related to post-operative vignetting. The system 10 may be employed in any procedure where sufficient pre-operative anatomic data is available to allow accurate tracing by the ray tracing module 26.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A system for predicting post-operative vignetting in an eye of a subject prior to implantation with an intraocular lens, the system comprising:
a controller having a processor and a tangible, non-transitory memory on which instructions are recorded;
a diagnostic module in communication with the controller, the diagnostic module being adapted to store pre-operative anatomic data of the eye as an eye model;
a projection module selectively executable by the controller, the projection module being adapted to determine imputed post-operative variables of the eye based at least partially on the pre-operative anatomic data and the intraocular lens;
a ray tracing module selectively executable by the controller, the ray tracing module being adapted to calculate propagation of light through the eye; and
wherein the controller is configured to:
obtain the pre-operative anatomic data of the eye, via the diagnostic module;
determine imputed post-operative variables of the eye, via the projection module, and incorporate the imputed post-operative variables into the eye model;
execute the ray tracing module to determine a light distribution for respective visual field angles across a predefined field of view in the eye model; and
determine one or more post-operative vignetting parameters based at least partially on the light distribution for the respective visual field angles.

2. The system of claim 1, wherein:
the ray tracing module traces a bundle of rays propagating through the eye; and
the one or more post-operative vignetting parameters include a first visual angle defined as a smallest of the respective visual field angles where at least a portion of the bundle of rays passing through a pupil of the eye will not pass through an optical zone of the intraocular lens.

3. The system of claim 2, wherein:
the one or more post-operative vignetting parameters include a second visual angle defined as the smallest of the respective visual field angles where the bundle of rays passing through the pupil will not pass through the optical zone of the intraocular lens.

4. The system of claim 3, wherein:
the one or more post-operative vignetting parameters include a third visual angle defined as the smallest of the respective visual field angles where the bundle of rays passing through the pupil will miss the intraocular lens entirely.

5. The system of claim 1, wherein:
the pre-operative anatomic data includes an axial length of the eye.

6. The system of claim 1, wherein:
the pre-operative anatomic data includes a respective location and a respective profile of an anterior corneal surface and a posterior corneal surface of the eye.

7. The system of claim 1, wherein:
the pre-operative anatomic data includes a location, an orientation, and a size of a pupil of the eye in a three-dimensional coordinate system, the pupil being under photopic conditions.

8. The system of claim 1, wherein:
the imputed post-operative variables of the eye include a respective location and a respective orientation of the intraocular lens.

9. The system of claim 1, wherein:
the imputed post-operative variables of the eye include a respective location and a respective orientation of a pupil and/or iris of the eye.

10. The system of claim 1, wherein:
the ray tracing module is adapted to trace a bundle of rays propagating posteriorly through the intraocular lens until reaching a retina of the eye; and
bundle of rays is focused to an infinitesimally small spot on the retina.

11. The system of claim 1, wherein:
the ray tracing module is adapted to employ respective refractive indices in the eye applicable to a wavelength of 550 nanometers of light.

12. A method for predicting post-operative vignetting in an eye of a subject prior to implantation with an intraocular lens, with a system having a controller with a processor and a tangible, non-transitory memory on which instructions are recorded, the method comprising:
adapting a diagnostic module to store pre-operative anatomic data of the eye as an eye model, via at least one imaging device;
adapting a projection module to determine imputed post-operative variables of the eye based at least partially on the pre-operative anatomic data and the intraocular lens, via the controller;
adapting a ray tracing module to calculate propagation of light through the eye, the ray tracing module being selectively executable by the controller;
obtaining pre-operative anatomic data of the eye, via the diagnostic module;
determining imputed post-operative variables of the eye, via the projection module, and incorporating the imputed post-operative variables into the eye model;
executing the ray tracing module to determine a light distribution for respective visual field angles across a predefined field of view in the eye model; and
determining one or more post-operative vignetting parameters based at least partially on the light distribution for the respective visual field angles.

13. The method of claim 12, wherein:
the ray tracing module traces a bundle of rays propagating through the eye; and
the one or more post-operative vignetting parameters include a first visual angle defined as a smallest of the respective visual field angles where at least a portion of the bundle of rays passing through a pupil of the eye will not pass through an optical zone of the intraocular lens.

14. The method of claim 13, wherein:
the one or more post-operative vignetting parameters include a second visual angle defined as the smallest of the respective visual field angles where the bundle of rays passing through the pupil will not pass through the optical zone of the intraocular lens.

15. The method of claim 14, wherein:
the one or more post-operative vignetting parameters include a third visual angle defined as the smallest of the respective visual field angles where the bundle of rays passing through the pupil will miss the intraocular lens entirely.

16. The method of claim 12, wherein:
the pre-operative anatomic data includes an axial length of the eye; and the pre-operative anatomic data includes a location, an orientation, and a size of a pupil of the eye in a three-dimensional coordinate system, the pupil being under photopic conditions.

17. The method of claim 12, wherein:

the imputed post-operative variables of the eye include a respective location and a respective orientation of the intraocular lens; and the imputed post-operative variables of the eye include a respective location and a respective orientation of a pupil and/or iris.

18. The method of claim 12, further comprising:

adapting the ray tracing module to trace a bundle of rays posteriorly through the intraocular lens until reaching a retina of the eye; and focusing the bundle of rays to an infinitesimally small spot on the retina.

* * * * *